US00PP29813P3

(12) United States Plant Patent
Di Primio

(10) Patent No.: US PP29,813 P3
(45) Date of Patent: Nov. 6, 2018

(54) ***CEREUS* PLANT NAMED 'PAOLINA'**

(50) Latin Name: *Cereus peruvianus*
Varietal Denomination: Paolina

(71) Applicant: Silvano Di Primio, Cepagatti (IT)

(72) Inventor: Silvano Di Primio, Cepagatti (IT)

(73) Assignee: W. Kordes Söhne Rosenschulen GmbH & Co. KG, Offenseth-Sparrieshoop ( * ) Notice: Subject to any disclaimer, the term of this patent is extended or adjusted under 35 U.S.C. 154(b) by 0 days.

(21) Appl. No.: 15/731,382

(22) Filed: Jun. 5, 2017

(65) Prior Publication Data

US 2018/0092278 P1 Mar. 29, 2018

(30) Foreign Application Priority Data

Sep. 27, 2016 (QZ) ..... PBR 2016/2331

(51) Int. Cl.
*A01H 5/00* (2018.01)
*A01H 5/02* (2018.01)
*A01H 5/04* (2018.01)

(52) U.S. Cl.
USPC ..... Plt./372
CPC ..... *A01H 5/02* (2013.01); *A01H 5/04* (2013.01)

(58) Field of Classification Search
USPC ..... Plt./372
See application file for complete search history.

*Primary Examiner* — Keith O. Robinson
(74) *Attorney, Agent, or Firm* — Samuel R. McCoy, Jr.

(57) ABSTRACT

A new and distinct *Cereus* cultivar named 'Paolina' which is characterized by a compact, freely branching growth habit, a fastigiate plant form, an abundance of dark green main stems with four prominent longitudinal ribs which give rise to many upright lateral branches, and very small quantity of soft, white spines on each plant. The claimed plant propagates successfully by softwood stem cuttings and has proven to be uniform and stable in the resulting generations.

3 Drawing Sheets

Latin name of the genus and species: The Latin name of the genus and species of the novel variety disclosed herein is *Cereus peruvianus*.

Variety denomination: The inventive variety of *Cereus peruvianus* disclosed herein has been given the variety denomination 'Paolina'.

CROSS REFERENCE TO RELATED APPLICATIONS

This application claims priority to the Community Plant Variety Rights application number 2016/2331, filed Sep. 27, 2016, which is herein incorporated by reference.

BACKGROUND OF THE INVENTION

Parentage: 'Paolina' originated as a naturally occurring, whole-plant mutation of *Cereus peruvianus* 'Florida' (not patented). In 2009, the inventor discovered the mutation at his commercial greenhouse in Place Chieti, Italy, growing amongst a crop of *Cereus peruvianus* 'Florida'. The mutation was noted for its compact habit, abundance of freely branching dark green stems and few soft spines and was isolated for further observation in order to confirm the distinctness and stability of the characteristics first observed. After further evaluation it was determined that the unique characteristics of the candidate plant would prove favorable for commercial marketability. The new variety was given the breeder denomination 'Paolina'.

Asexual Reproduction: In 2009, 'Paolina' was first asexually reproduced in Place Chieti, Italy by way of softwood stem cuttings. The claimed plant was found to asexually reproduce in a uniform and stable manner and 11 successive cycles of vegetative propagation have proven it to be true to type.

SUMMARY OF THE INVENTION

The following characteristics have been repeatedly observed and represent the distinguishing characteristics of the new *Cereus* cultivar 'Paolina'. These traits, in combination, distinguish 'Paolina' as a new and distinct cultivar.

1. 'Paolina' exhibits a compact, freely branching growth habit and a fastigiate plant form; and
2. 'Paolina' exhibits an abundance of dark green main stems, each with four prominent longitudinal ribs, and
3. 'Paolina' exhibits areoles borne along the entire length of the four longitudinal ribs of the main stems; and
4. 'Paolina' exhibits immature areoles encircled by tufts of soft white hairs, and occasionally giving rise to a soft, white spine; and
5. 'Paolina' exhibits very few spines per plant; and
6. 'Paolina' exhibits areoles which develop into upright lateral branches as main stems mature.

BOTANICAL DESCRIPTION OF THE PLANT

Figure 1:
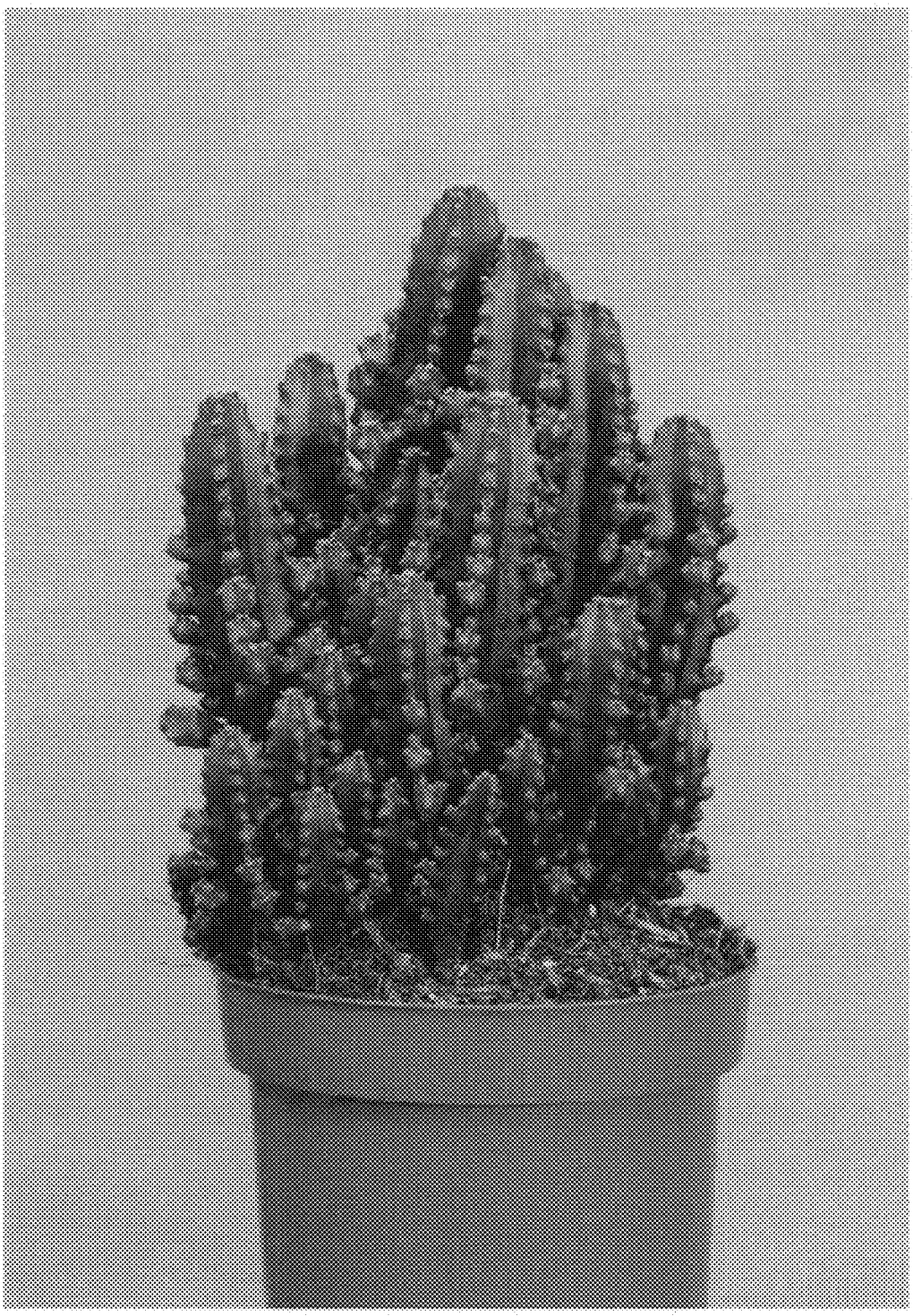
FIG. 1 illustrates, as nearly true as it is reasonably possible to make the same in color photographs of this type, an exemplary 10 month old greenhouse-grown 'Paolina' plant in Place Chieti, Italy.
Figure 2:
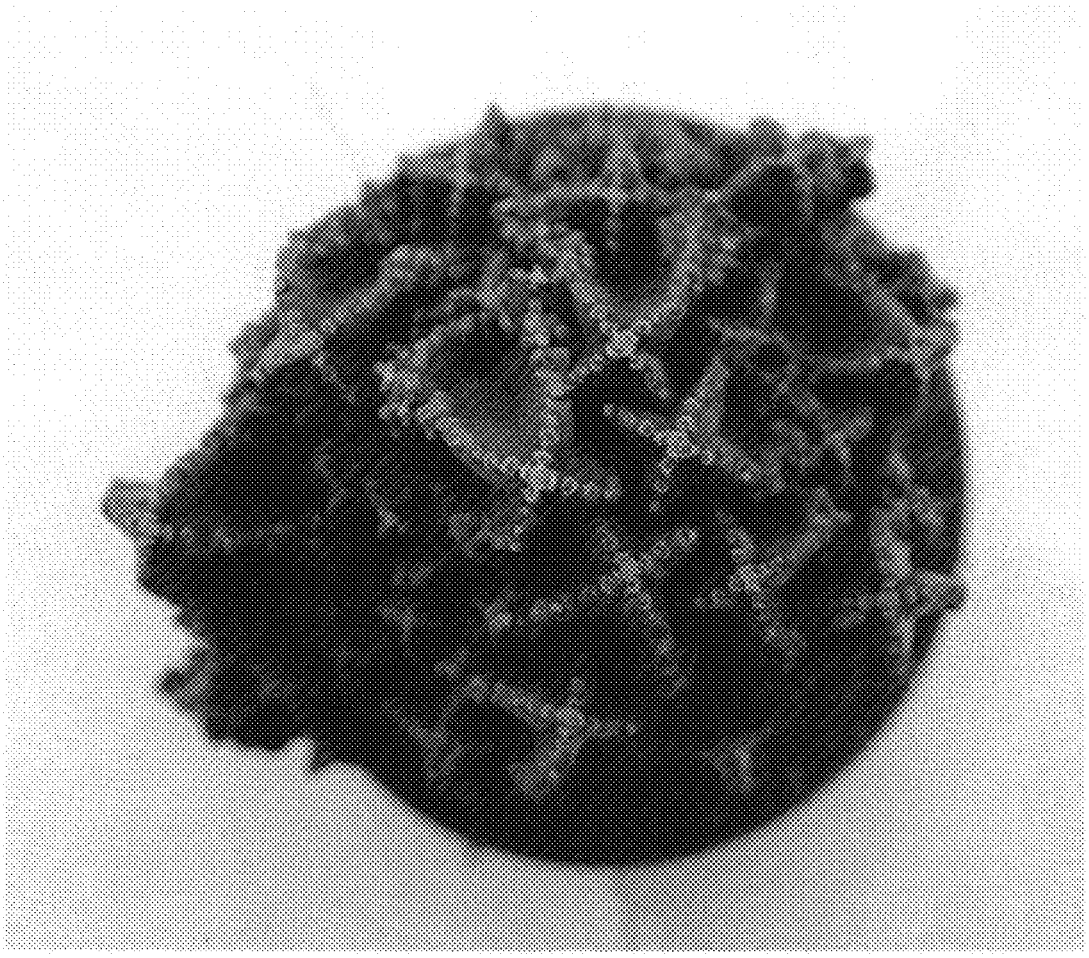
FIG. 2 illustrates, as nearly true as it is reasonably possible to make the same in color photographs of this type, an aerial view of the plant from FIG. 1.
Figure 3:
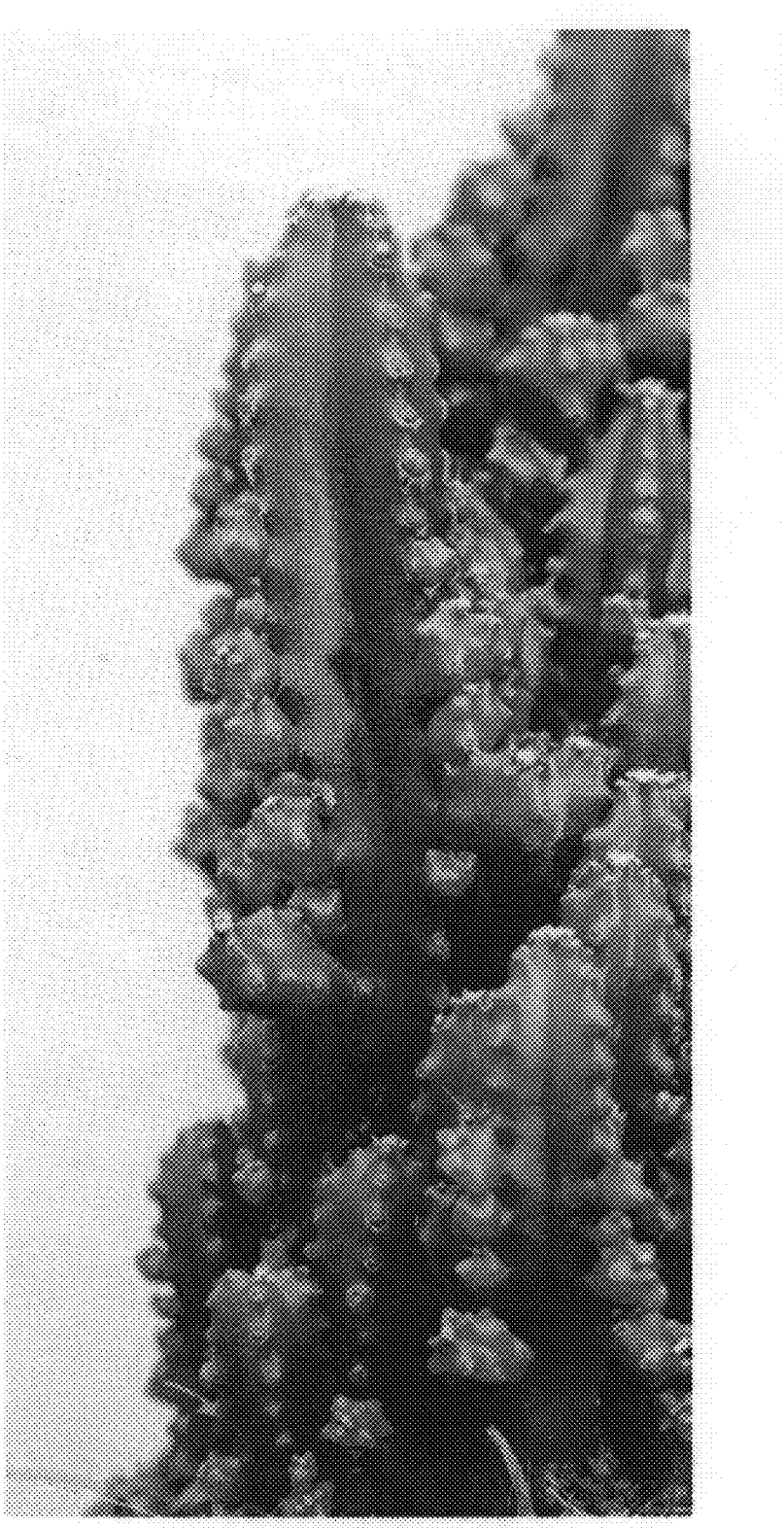
FIG. 3 illustrates, as nearly true as it is reasonably possible to make the same in color photographs of this type, a typical main stem of 'Paolina'.

The following observations and measurements made in April of 2017 describe averages from a sample set of six specimens of 10 month old 'Paolina' plants grown in 12 cm nursery containers at a greenhouse in Place Chieti, Italy. Plants were produced using conventional greenhouse production protocols for *Cereus* which consisted of full sun exposure, regular irrigation, and fertilizer applications as needed. No chemical pest control measures were taken, and no photoperiodic treatments or artificial light was given to the plants.

Those skilled in the art will appreciate that certain characteristics will vary with older or, conversely, younger plants. 'Paolina' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2015 (sixth edition).

A botanical description of 'Paolina' and comparisons with the presumed parents are provided below.

General plant description:

*Plant habit.*—Perennial succulent cactus.

*Plant form.*—Upright; fastigiated; compact.

*Height.*—17.1 cm.

*Width.*—11.7 cm.

*Rate of growth.*—Low.

*Plant vigor.*—Low.

*Environmental tolerances.*—Adapt to, at least, USDA Zones 10 to 13 and temperatures as high as 40 degrees Celsius; low tolerance to rain; high tolerance to wind.

*Pest and disease susceptibility or resistance.*—Plants have not been observed to be susceptible or resistant to pathogens and pests common to *Cereus*.

*Propagation.*—Propagation is accomplished using softwood stem cuttings.

*Time to develop roots.*—Approximately 35 days, at approximately 21 degrees Celsius.

*Crop time.*—Approximately 10 months are needed to produce a marketable 12 cm pot in Place Chieti, Italy.

Root system:

*Description.*—Fleshy, tuberous taproots give rise to fibrous secondary roots; sparsely branched and deeply rooted.

Stems:

*Branching habit.*—A plurality of erect main stems with areoles developing into upright lateral branches. Main stems — Quantity — 52. Attitude — Erect; approximately 10 degrees from vertical. Cross section — Longitudinally ribbed; 4 prominent symmetric ribs. Length — 94 mm. Diameter — 18 mm. Internode length — 4 mm. Color of juvenile stem — Green, RHS 143B. Color of mature stem — Green, RHS NN137A. Color at the nodes — Green, RHS NN137A. Texture and luster — Smooth, glabrous and slightly glossy. Strength — Strong. Lateral branches — Quantity — Approximately 16 areoles per main stem develop into lateral branches; approximately 800 per plant. Branch angle to main axis — Less than 45 degrees; becoming more erect with age. Cross-section — Globular and somewhat angular; becoming longitudinally ribbed with 4 symmetric ribs as the lateral branches mature. Areoles are also present on lateral branches. Length — 9.0 mm. Diameter — 7.0 mm. Internode length — 2 mm. Color of juvenile stem — Green, RHS 143B. Color of mature stem — Green, RHS NN137A. Color at the nodes — Green, RHS NN137A. Texture and luster — Smooth, glabrous and slightly glossy. Strength — Strong. Areoles — General — Areoles arise approximately every 4 mm along the entire length of the axial ribs of the main stems. Juvenile areoles are approximately 2 mm high and 1 mm in diameter and will eventually develop into lateral branches as stems mature. Areoles are encircled by tufts of very short, soft hairs of approximately 1 mm long and colored greyed-white, nearest to RHS 156D. Approximately one in every ten juvenile areoles will give rise to a spine.

Spines:

*Attachment.*—Growing from areoles.

*Arrangement.*—Alternate.

*Quantity.*—Less than 1 spine per 10 areoles.

*Division.*—Simple.

*Shape.*—Spine-like; pungent.

*Cross section.*—Rounded.

*Length.*—4.0 mm.

*Width.*—0.1 mm.

*Apex.*—Pungent.

*Base.*—Cuneate.

*Margin.*—No margins; spines are round.

*Aspect.*—Upward and outward.

*Texture and luster, adaxial surface.*—Smooth, glabrous, and slightly to moderately glossy.

*Texture and luster, abaxial surface.*—Smooth, glabrous and slightly glossy.

*Strength.*—Somewhat weak.

*Color.*—Juvenile spines, adaxial surface — Yellow-white, nearest to RHS 158D. Juvenile spines, abaxial surface — Yellow-white, nearest to RHS 158D. Mature spines, adaxial surface — Yellow-white, nearest to RHS 158D, and suffused with greyed-yellow towards the base, nearest to in between RHS 161B and 161C. Mature spines, abaxial surface — Yellow-white, nearest to RHS 158D, and suffused with greyed-yellow towards the base, nearest to in between RHS 161B and 161C.

*Venation.*—No visible venation.

Inflorescence: Flowers not observed.

Flower bud: Not observed.

Flower: Not observed.

Reproductive organs: Not observed.

Fruit and seed: Not observed.

COMPARISON WITH THE PRESUMED PARENT PLANT

Plants of the new cultivar 'Paolina' differ from the seed parent, *Cereus peruvianus* 'Florida' (not patented), by the characteristics described in Chart 1.

CHART 1

| Characteristic | 'Paolina' | 'Florida' |
|---|---|---|
| Plant size. | Compact. | Less compact. |
| Abundance of stems. | More abundant. | Less abundant. |
| Number of longitudinal ribs on main stems. | Four. | More than four. |
| Stem color. | Darker green. | Lighter green. |
| Abundance of spines. | Very few spines. | Abundant. |
| Strength of spines. | Somewhat weak; thin diameter; less painful to the touch. | Stronger than those of 'Paolina'; thicker diameter; more painful to the touch. |
| General coloration of spines. | Lighter color. | Darker color. |

COMPARISON WITH THE MOST SIMILAR *CEREUS* CULTIVAR KNOWN TO THE INVENTOR

Plants of the new cultivar 'Paolina' are most similar to the commercial variety *Cereus hildmannianus* subsp. *uruguayanus* (not patented). A comparison of 'Paolina' with *Cereus hildmannianus* subsp. *uruguayanus* is described in Chart 2.

CHART 2

| Characteristic | 'Paolina' | *Cereus hildmannianus* subsp. *uruguayanus* |
|---|---|---|
| Plant size. | Compact. | Less compact. |
| Abundance of stems. | More abundant. | Less abundant. |
| Number of longitudinal ribs on main stems. | Four. | Five. |
| Abundanceb of spines. | Very few spines. | More abundant. |
| Strength of spines. | Somewhat weak. | Stronger than those of 'Paolina'. |

That which is claimed is:

1. A new and distinct variety of *Cereus peruvianus* plant named 'Paolina', substantially as described and illustrated herein.

* * * * *